(12) United States Patent
Schon et al.

(10) Patent No.: US 7,238,190 B2
(45) Date of Patent: Jul. 3, 2007

(54) SURGICAL APPARATUS TO ALLOW REPLACEMENT OF DEGENERATIVE ANKLE TISSUE

(75) Inventors: Lew C. Schon, Baltimore, MD (US); Brent G. Parks, West Friendship, MD (US); Christopher Chiodo, Walpole, MA (US)

(73) Assignee: Concepts In Medicine III, LLC, West Friendship, MD (US)

( * ) Notice: Subject to any disclaimer, the term of this patent is extended or adjusted under 35 U.S.C. 154(b) by 355 days.

(21) Appl. No.: 10/403,243

(22) Filed: Mar. 28, 2003

(65) Prior Publication Data

US 2004/0193169 A1 Sep. 30, 2004

(51) Int. Cl.
*A61F 5/00* (2006.01)
*A61B 17/58* (2006.01)

(52) U.S. Cl. .......................................... 606/87; 606/88

(58) Field of Classification Search ................ 606/87, 606/102, 96, 79, 80, 86, 88, 167, 89; 623/21.11, 623/21.18
See application file for complete search history.

(56) References Cited

U.S. PATENT DOCUMENTS

| | | | | |
|---|---|---|---|---|
| 4,952,213 A | * | 8/1990 | Bowman et al. ............... 606/79 |
| 5,190,547 A | | 3/1993 | Barber et al. .................. 606/79 |
| 5,540,692 A | | 7/1996 | Tidwell ........................ 606/79 |
| 5,569,260 A | * | 10/1996 | Petersen ........................ 606/88 |
| 5,628,749 A | * | 5/1997 | Vendrely et al. ............... 606/80 |
| 5,649,928 A | | 7/1997 | Grundei ........................ 606/88 |
| 5,681,316 A | * | 10/1997 | DeOrio et al. ................ 606/88 |
| 5,681,320 A | | 10/1997 | McGuire ..................... 606/104 |
| 5,766,259 A | | 6/1998 | Sammarco .................... 623/21 |
| 5,993,453 A | | 11/1999 | Bulara et al. ................. 606/79 |
| 6,190,390 B1 | * | 2/2001 | McAllister .................... 606/87 |
| 6,205,411 B1 | | 3/2001 | DiGioia et al. ............... 703/11 |
| 6,228,089 B1 | | 5/2001 | Wahrburg ..................... 606/86 |
| 6,254,605 B1 | | 7/2001 | Howell ........................ 606/96 |
| 6,267,762 B1 | | 7/2001 | Millard et al. ................ 606/54 |
| 2004/0002768 A1 | * | 1/2004 | Parks et al. .............. 623/21.18 |

* cited by examiner

*Primary Examiner*—Pedro Philogene
(74) *Attorney, Agent, or Firm*—Larry J. Guffey

(57) ABSTRACT

A surgical apparatus that makes possible the replacement of ankle tissue between the bottom of the tibia and the adjoining top of the talus bone comprises: (a) a base having primary and secondary anchoring holes that extend through the base and through which anchoring pins may be extended for anchoring withh the tibia, anchoring holes having adjoining and cooperating, threaded, set screw holes and set screws that cooperate to assist in fixing the position of the base relative to the anchoring pins and the tibia, (b) a surgical blade positioning shelf, the front surface of the shelf configured to approximate the curvature observable in the top portion of the talus and the rear surface of the shelf having attached to it a shaft which may slide in and out from an opening in the front surface of the base, and (c) indicia attached to the shaft which allows one to record the position of the front surface of the surgical blade positioning shelf relative to the base.

16 Claims, 6 Drawing Sheets

SURGICAL APPARATUS TO ALLOW REPLACEMENT OF DEGENERATIVE ANKLE TISSUE

BACKGROUND OF THE INVENTION

1. Field of the Invention

This invention relates to orthopedic surgical instruments and procedures. More particularly, this invention relates to an orthopedic surgical apparatus that makes possible the surgical replacement of degenerative ankle tissue between the bottom of the tibia and the adjoining top of the talus bone.

2. Description of the Related Art

Many people today are involved in a sport or some other type of physical activity. Some of these activities involve a low risk of chance of injury to one's joints, such as walking and swimming, while others involve a high risk of injury, such as football and ballet dancing.

Primarily as a result of these activities, injured and diseased joints are a common occurrence for an ever increasing number of people. One of the most commonly afflicted joints is the ankle joint, withh arthritis of the ankle being a frequent problem for many people.

Arthritis of the ankle is a condition in which the tissue surfaces between the bottom of the tibia and the adjoining top of the talus bone becomes diseased or worn. People afflicted withh this condition often experience great pain when walking, or doing any activity that requires movement of the foot. Eventually the pain from this condition becomes so severe that often some form of ankle surgery is required to alleviate it.

In recent years, conventional orthopedic surgical procedures have consisted of either fusing the ankle and lower leg bone together withh pins, or replacing a section of the affected tissue withh a metal-polymer prosthesis. See U.S. Pat. No. 5,766,259.

Both of these approaches have their drawbacks. For example, in fusion there is a loss of motion in the ankle joint which may cause difficulties withh other associated parts of the leg, such as the knee joint and more distal joints in the hindfoot. Meanwhile, replacing the affected tissue withh a metal-polymer member has resulted in cases where bone has failed to grow into crevices along the metal-bone interface thereby causing considerable pain for the patient and result in the lifespan of such a prosthesis being diminished to only a few years or less.

Recent advancements in biomedical engineering, which have overcome many of the problems associated withh the body's rejection of foreign materials, have now made it possible to consider using cadaverous ankle tissue in place of the metal-polymer, prosthesis materials. The present invention resulted from medical research directed to the development of the means and procedures for replacing the affected tissue in injured and diseased ankle joints withh healthy, cadaverous ankle tissue. These new means and procedures should make a significant contribution to the continuing need for the development of better means of treating ankle joint injuries and diseases.

3. Objects and Advantages

As a means to better understand the present invention, it is instructive to also consider the objects and advantages of the present invention.

It is an object of the present invention to provide an apparatus that facilithates a surgical procedure where it is desired to cut a bone so as to have a prescribed degree of curvature in the cut bone.

It is an another object of the present invention to provide a better means of treating ankle joint injuries and diseases.

It is an yet another object of the present invention to provide an apparatus that facilithates a surgical procedure involving the replacement of ankle tissue between the bottom of the tibia and the adjoining top of the talus bone.

It is an object of the present invention to provide a means that facilithates replacing the injured and diseased tissue of ankle joints withh healthy, cadaverous tissue.

It is a further object of the present invention to provide a means for replacing the injured and diseased tissue of ankle joints in such a manner that lesser amounts of tissue have to be resected from the ankle.

It is a still further object of the present invention to provide a means for replacing the injured and diseased tissue of ankle joints in such a manner that the replacement tissue will have a minimal risk of being rejected.

These and other objects and advantages of the present invention will become readily apparent, as the invention is better understood by reference to the accompanying drawings and the detailed description that follows.

SUMMARY OF THE INVENTION

Recognizing the need for the development of better means of treating ankle joint injuries and diseases, the present invention is generally directed to satisfying the needs set forth above and overcoming the disadvantages identified withh prior art surgical devices and procedures.

In accordance withh one preferred embodiment of the present invention, the foregoing need can be satisfied by providing an apparatus that makes possible the surgical replacement of ankle tissue between the bottom of the tibia and the adjoining top of the talus bone. This apparatus comprises: (a) a base having primary and secondary anchoring holes that extend through the base and through which anchoring pins may be extended for anchoring withh the tibia, anchoring holes having adjoining and cooperating, threaded, set screw holes and set screws that cooperate to assist in fixing the position of the base relative to the anchoring pins and the tibia, (b) a surgical blade positioning shelf, the front surface of the shelf configured to approximate the curvature observable in the top portion of the talus and the rear surface of the shelf having attached to it a shaft which may slide in and out from an opening in the front surface of the base, and (c) indicia attached to the shaft which allows one to record the position of the front surface of the surgical blade positioning shelf relative to the base.

According to a second embodiment of the present invention, a method is provided for facilithating a surgical procedure where it is desired to cut a bone so as to have a prescribed degree of curvature in the cut bone. The method comprises the steps of: (a) providing a base for attachment to the bone, (b) removably attaching the base to the bone, (c) providing an interchangeable, surgical blade positioning means for attachment to the base, (d) configuring the surgical blade positioning means so that it has a front surface configured to have the prescribed degree of curvature and to allow a surgeon to position a surgical blade for making the cut having the prescribed degree of curvature, (e) attaching the surgical blade positioning means to the base in such a manner so as to provide flexibility in the orienthation of the front surface of the surgical blade positioning means, and (f) attaching an indicia means to the surgical blade positioning means so as to allow one to precisely determine the position of the front surface of surgical blade positioning means relative to the base.

Thus, there has been summarized above, rather broadly, the present invention in order that the detailed description that follows may be better understood and appreciated. There are, of course, additional features of the invention that will be described hereinafter and which will form the subject matter of the claims to this invention.

DESCRIPTION OF THE PREFERRED EMBODIMENT

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

For the approach of replacing the diseased tissue in ankle joints withh healthy ankle tissue to be successful, considerable care has to be taken to ensure that bony in-growth between the involved bones is maximized. This leads to two requirements for such surgery: (1) the cadeveric ankle pieces must fit as exactly as possible inside the void left by the resected or removed ankle tissue, and (2) the foreign bone mass must be minimized in order to lessen the body's risk of rejecting the implanted material.

Figure 1:
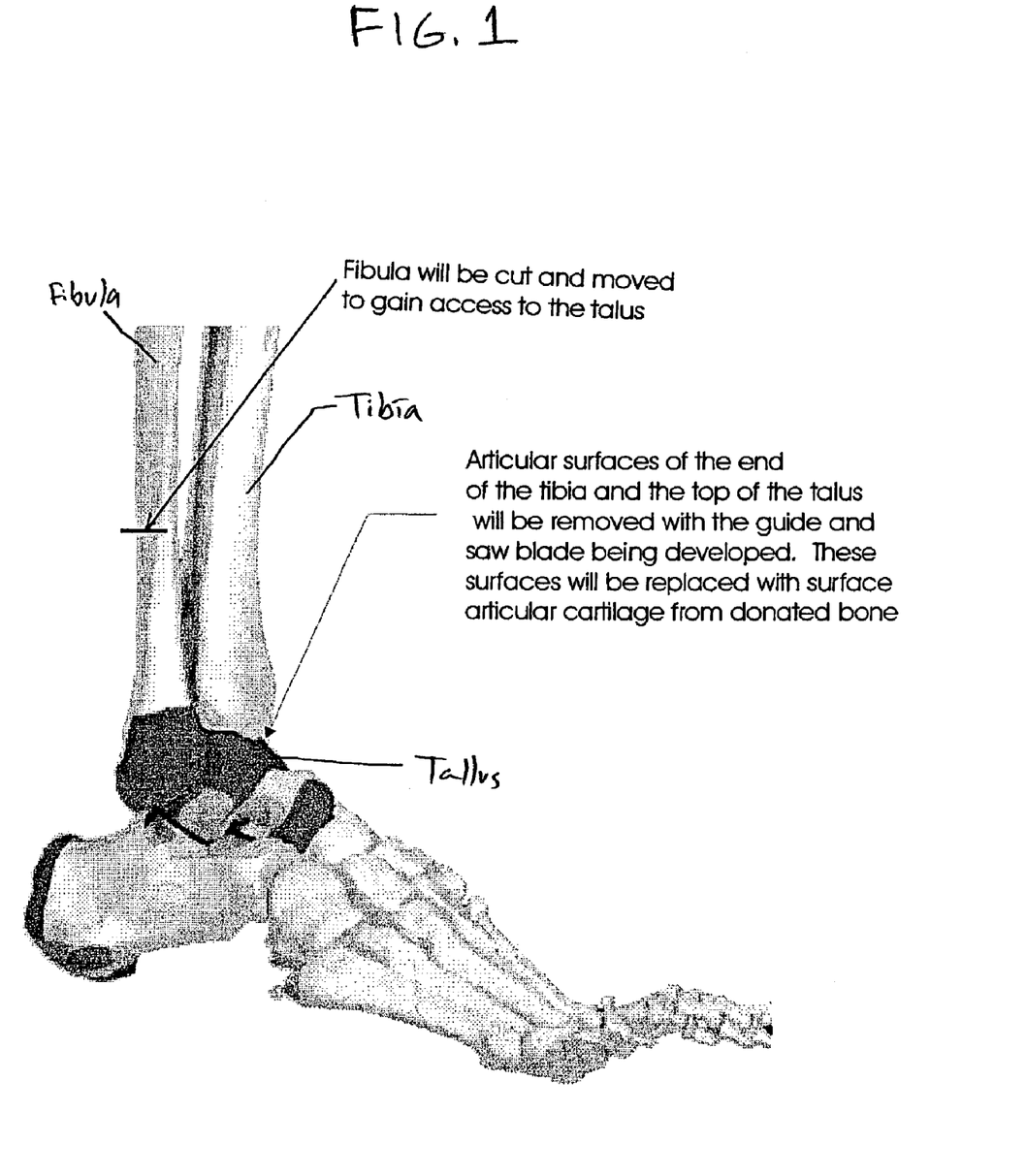
FIG. 1 provides a lateral or instep-side of the ankle view of the ankle joint.

The current surgical procedures for replacing a section of the affected tissue withh a metal-polymer prosthesis usually involves approaching the joint from the anterior or front of the leg and using a straight blade and three incisions. See FIG. 1 for a lateral or instep-side of the ankle view of the angle joint.

In the research for the development of the present invention, it was found that the amount of resected bone in such allograft procedures could be minimized if the resected bone were to be removed withh a curved saw blade that approached the joint from the lateral or instep-side of the ankle. This allows a cut to be used that duplicates the curvature seen on the talus' exterior surface in the affected area. It can be seen that, withh this lateral approach to the ankle joint, it is necessary that the fibula be cut and the lower portion of it be moved out of the way in order to provide direct access to the ankle joint.

Figure 2A:
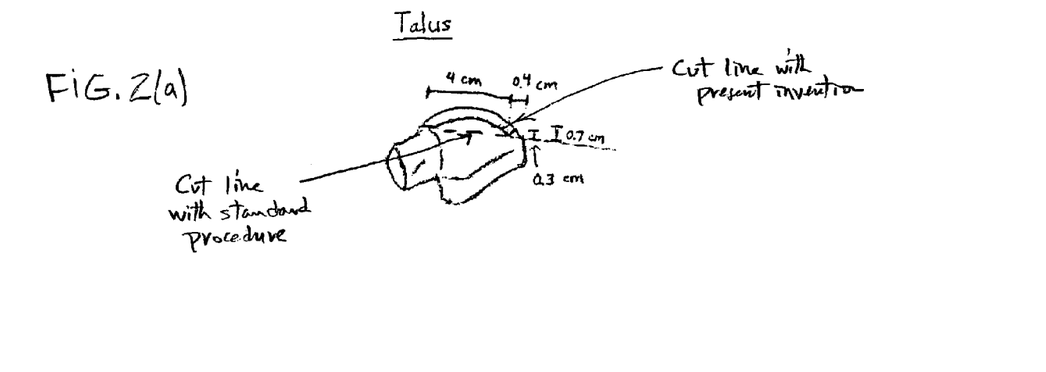
FIG. 2(a) is a lateral side view of the talus and shows by solid and dashed lines, respectively, the surgical cuts that would be made using the present invention and those that are made using current ankle allograph techniques.
Figure 2B:
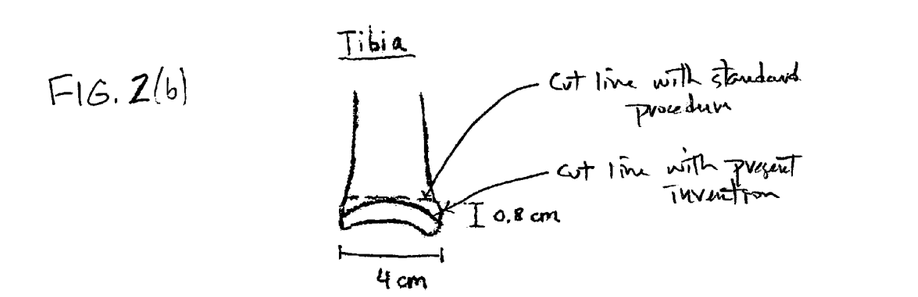
FIG. 2(b) is a lateral side view of the tibia and shows by solid and dashed lines, respectively, the surgical cuts that would be made using the present invention and those that are made using current ankle allograph techniques.
Figure 2C:
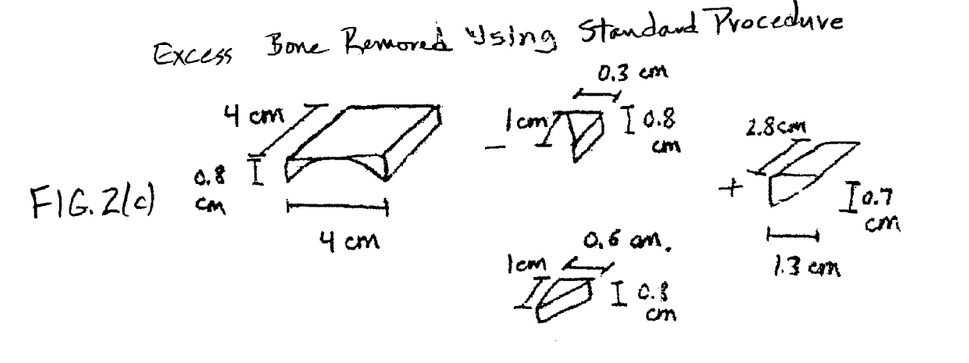
FIG. 2(c) illustrates the excess bone that is not removed using the surgical procedure of the present invention as compared the mass of bone removed using current ankle allograph techniques.

FIGS. 2(a)–2(c) provide some information on the resected bone mass reduction than can be achieved withh using a curved blade rather than a straight blade for the cuts on both the talus and the tibia. If the width and height of the affected area are approximately 4 cm and 0.8 cm, respectively, and the removed sections have a uniform thickness of approximately 0.3 cm, it is estimated that approximately 11.4 cm$^3$ less bone needs to be resected using the surgical procedure of the present invention.

Figure 3:
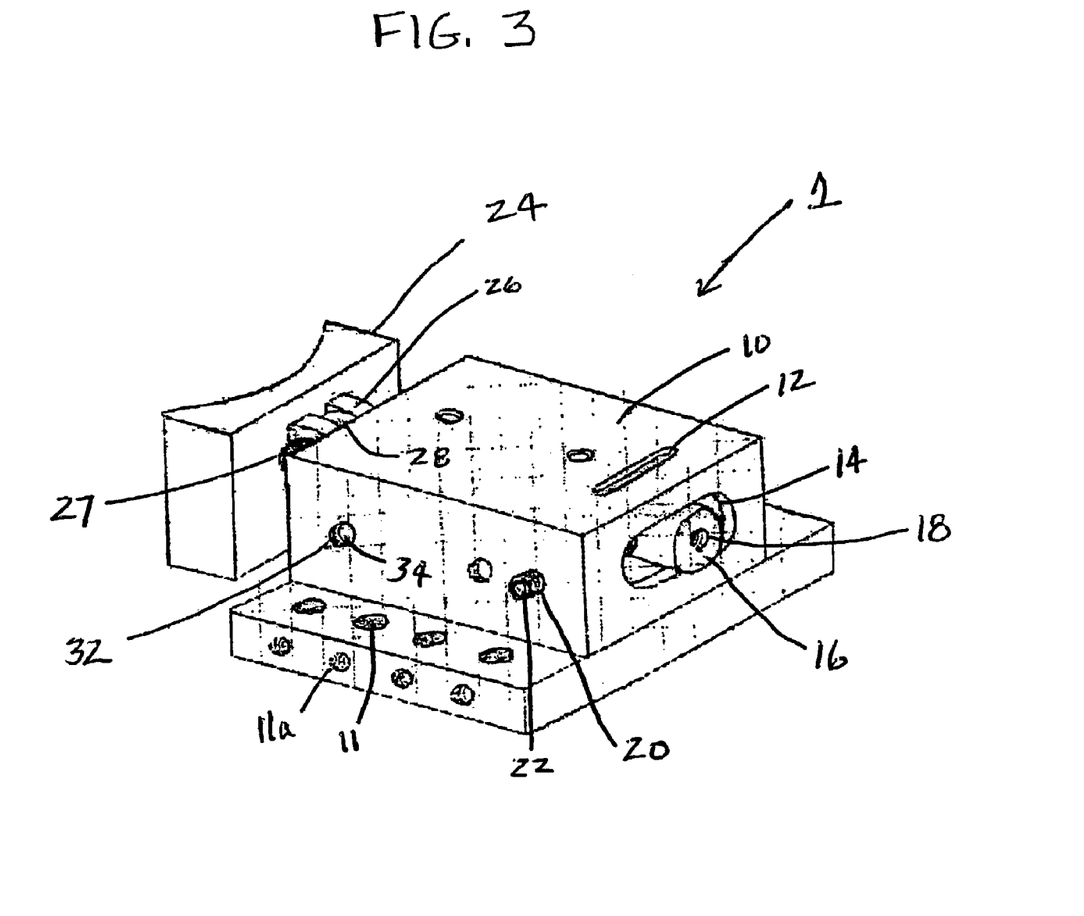
FIG. 3 is a perspective, side view of a preferred embodiment of the present invention.

Referring now to the FIG. 3 which shows a preferred embodiment of the present invention, and wherein like reference numerals in this and the subsequent drawings designate like elements throughout. FIG. 3 shows a surgical apparatus 1 that is comprised of a base 10 which has a plurality of secondary anchoring holes 11 through which one or more anchoring or mounting pins may be extended for anchoring withh the patient's tibia. Set screw holes 11a in the side of the base allow set screws to be used to fix the position of the base relative to the pins that extend from the patient's tibia. The slotted hole 12 on the top of the base is placed over a mounting pin in the patient's tibia to provide a primary or preferred initial means for securing the base to the patient's tibia.

At the back of the base, a slotted cavity 14 has been provided to allow for the placement of a locking cylinder 16 in the base 10. The locking cylinder fits withhin this cavity withh its distal end generally extending toward the front of the base. This cylinder has a hole that extends from its exterior surface and intersects a threaded bore 18 that extends along the axis of the cylinder from the cylinder's proximate end which is exposed in the entrance to base's rear cavity. The slotted hole 12 on the top of the base extends into the cavity 14 created in the rear of the base and then through the bottom portion of the base, so that this slotted hole 12 extends all the way through the base.

Figure 4:
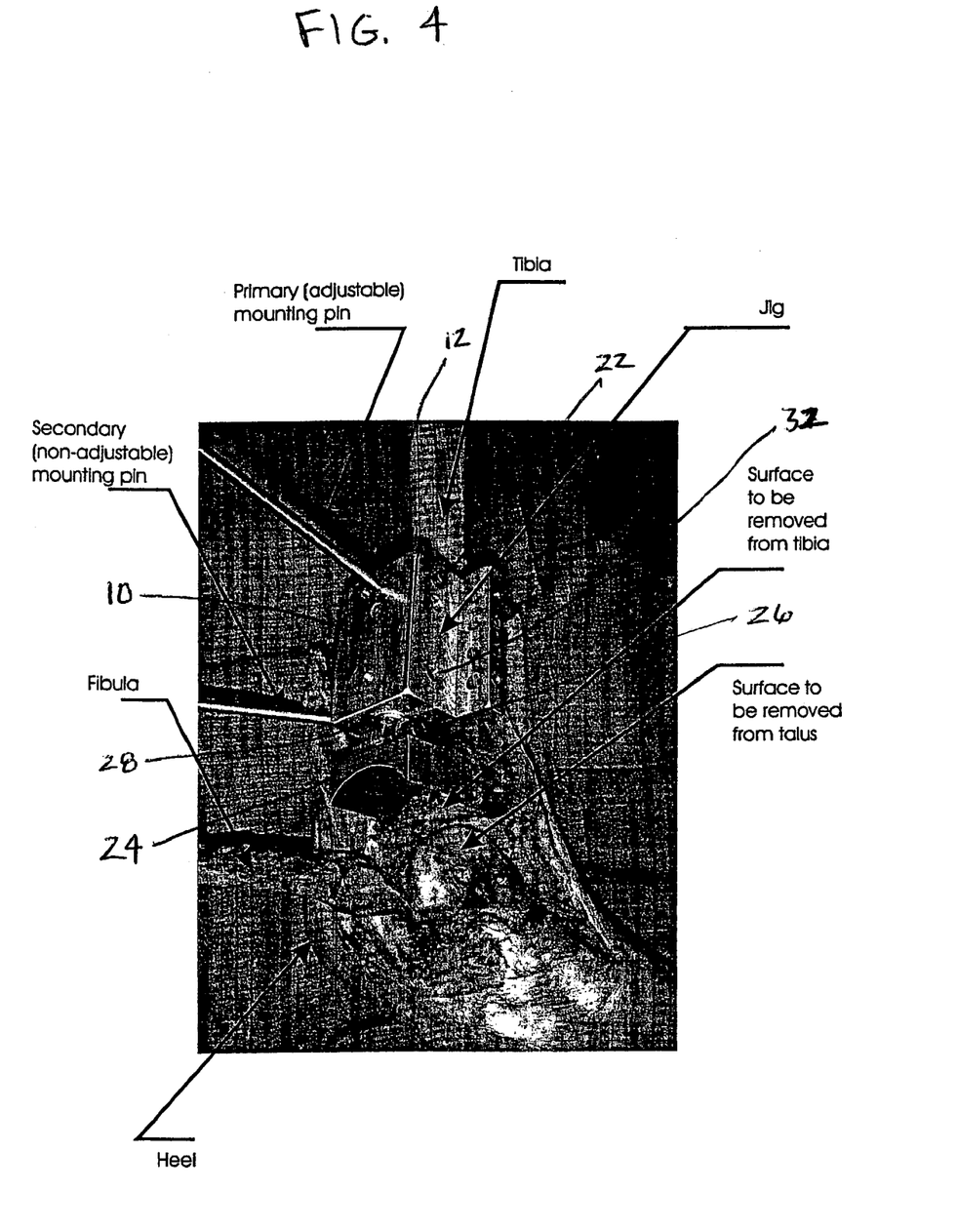
FIG. 4 shows a preferred embodiment of the present invention in use for surgically removing a portion of the adjoining tissue between the top of the talus and the bottom of the tibia.

In use, see FIG. 4, the cylinder 16 is placed such that the pin from the patient's tibia also extends through the hole in the cylinder's exterior surface. The cylinder is secured to the pin by a set screw that fits withhin the cylinder's threaded, axial bore 18 and can be turned by accessing the set screw's free end which is exposed at the cylinder's proximate end. From each side of the base extend additional threaded bores 20 that project into the sides of the bases' rear cavity 14. These bores contain set screws 22 that can be tightened to lock the cylinder 16 in place relative to the rest of the base 10. The advantage of this configuration is that it provides the surgeon withh a means to adjust the location of the base 10 relative to the locking cylinder 16 which is locked to the pin in the patient's tibia. Thus, the locking cylinder 16 can be moved to either side or rothated about a vertical axis defined by the axis of the pin that extends from the patient's tibia. This allows precise alignment of the shelf 24 withh the bones to be cut (tibia and talus).

Figure 5:
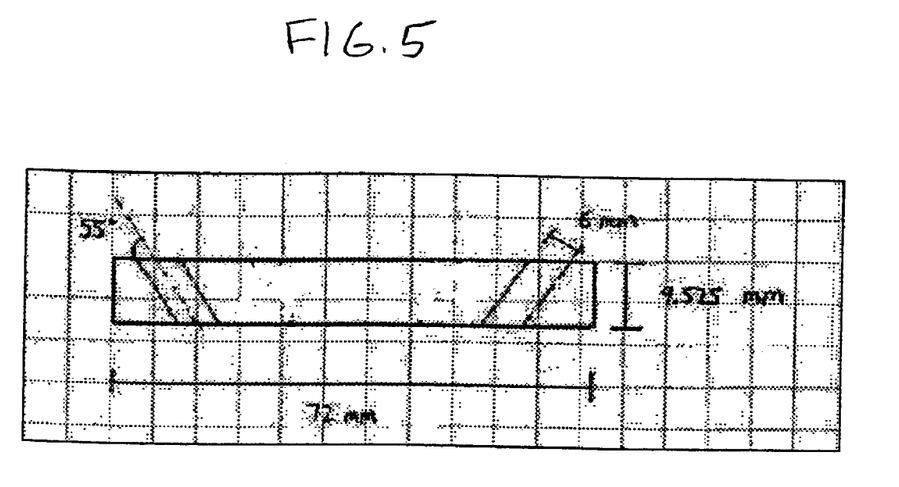
FIG. 5 shows a side view of the lower part of the base and its edges holes that slant towards the base's longitudinal centerline.

The centerlines of the anchoring holes 11 which are located in the base's top surface and towards its outer edges are slanted towards and at an angle withh respect to the base's longitudinal centerline. This angle is provided so as to allow the pins that pass through these holes to approximately contact the tibia perpendicularly to its surface. This allows these pins to be directed towards the tibia's centerline so as to provide the pins withh the most secure attachment to the bone. For a preferred embodiment of the present invention that has a base whose width and heigth are 72 mm and 9.5 mm, respectively, and whose edge holes are 7 mm from the edges, a preferred slant angle for these edge holes is in the range of 50–60 degrees. See FIG. 5.

Figure 6:
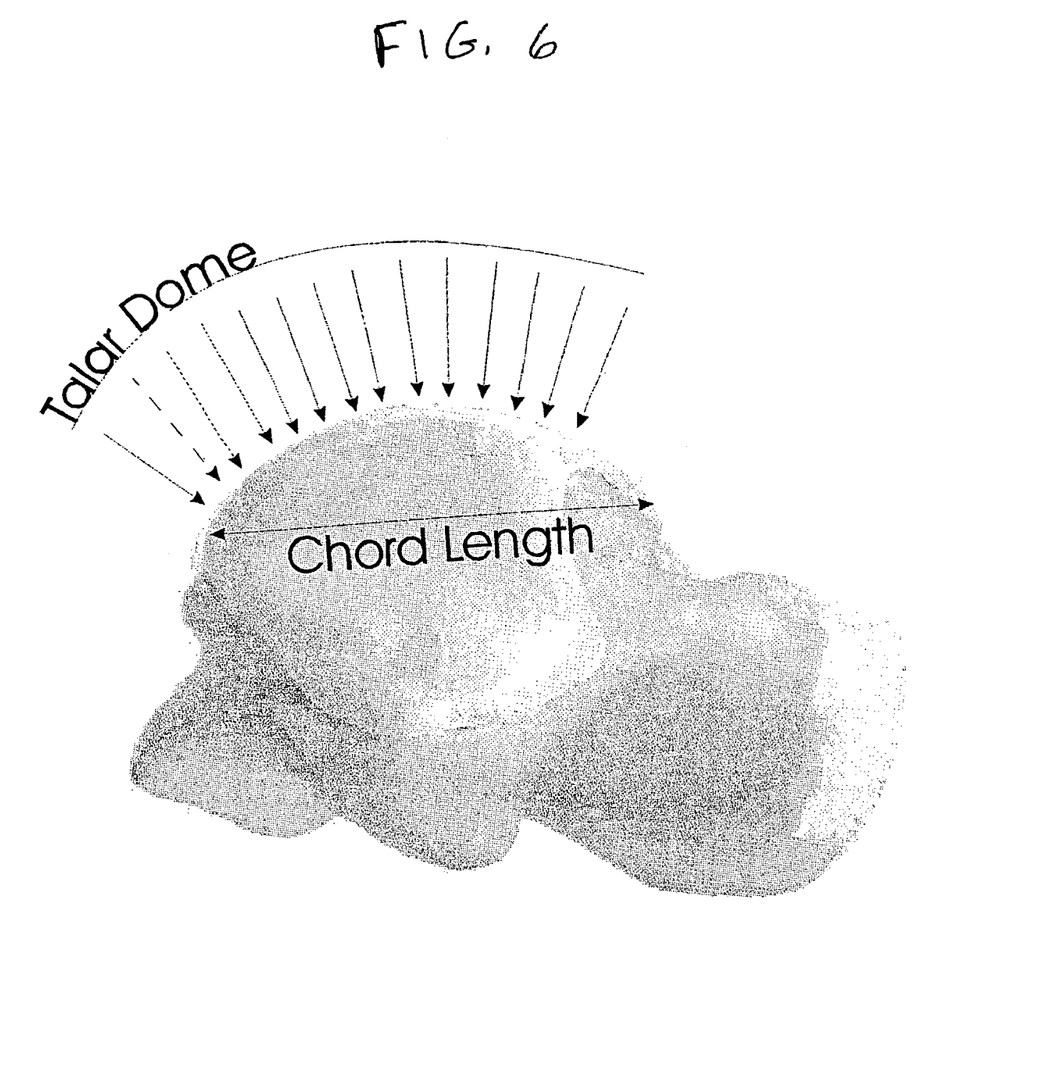
FIG. 6 is an illustration of the dome or top surface of a typical talus bone which shows the curvature of this surface.
Figure 7:
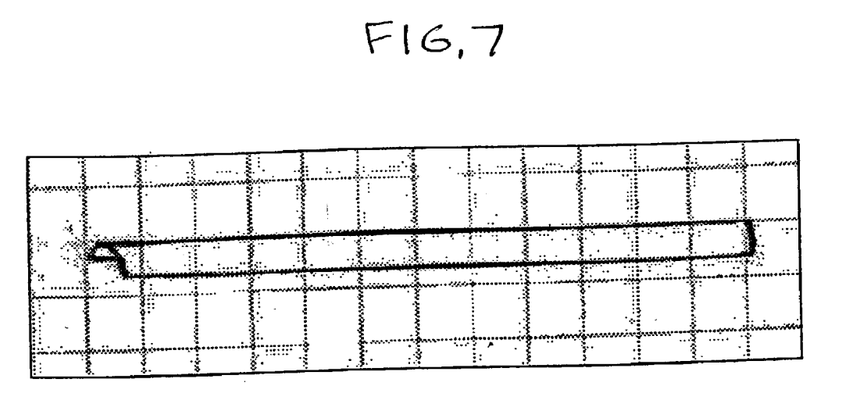
FIG. 7 illustrates the curved blade that a surgeon uses withh the present invention.

To the front of this base 10 is attached a shelf 24; the front surface of which is shaped so as to have a curvature that is similar to that found on the top of the typical talus surface. See FIG. 6. Measurements of a number of ankle joints suggests that the shelf's radius of curvature should in the range of 15.5–20.5 mm. The surgeon places his curved blade, see FIG. 7, against the shelf's front surface to guide his cutting during the surgical procedure.

The shelf 24 is mounted so that it can be pivoted up and down about a pivot joint 26 which is mounted on the back of the shelf. A set screw 27 allows the angular rothation of the pivot joint 26 to be fixed. Additionally, the nature of this connection is such that the shelf can easily be detached from the shaft. This allows for the opportunity to interchange the shelf that is attached to a shaft so that a shelf can be selected from a group of those having various degrees of surface curvature so as to utilize the shelf having the optimum degree of curvature.

From the shelf's pivot joint, there extends a shaft 28 which can slip into and out of a cavity that exists in the front of the base. On the side of the base there exist two additional bores 32 in which are placed set screws 34 that can be screwed inward so as to contact the exterior surface of the shaft 28 that extends into the base's front cavity. Thus, the distance between the back of the shelf and the front of the base can be set by the use of these set screws to lock the shaft relative to the base.

With this configuration, the shelf's position is adjustable in three directions: forward and backward as the shaft moves in and out of the base, rothationally about the axis of the shaft which can rothate withhin the base's front cavity, and rothationally (i.e., up and down, assuming that the ends of the shelf are extending horizontally) about the hinge joint that connects the front of the shaft and the back of the shelf. This degree of flexibility in the location of the shelf, even after the base has been fixed to the patient's tibia, is very important in the attainment of exact duplicate cuts on an ankle joint.

From experimenthation withh various early prototypes of this apparatus, it was found advisable to make the height of the shelf 24 as large as possible to provide the best foundation on which the surgeon could rest his blade when making the necessary cuts. Another feature of the preferred embodiment shown in FIG. 2 is that the space around the shelf's front surface is totally open. This allows the surgeon maximum visibility and the opportunity to clearly see and have access to the bones in the area of the ankle joint.

To aid the surgeon in making the most precise cuts possible, a measuring scale or indicia 36 is provided on the shaft 28 so that its extension distance from the front surface of the base can be easily noted and recorded as an aid in later repeating the setup of the apparatus to make the necessary duplicate cuts.

After the necessary incisions have been made to expose the ankle joint and the fibula has been cut and peeled back to allow full access to the joint, the apparatus 1 is placed on the tibia at the location where its shelf 24 can best be utilized in making the necessary cuts on the talus and the tibia. The orienthation above the tibia of the base's top, slotted hole 12 serves to define the site for the drilling of a hole for the insertion of a primary mounting pin in the tibia. After this pin is inserted, its extended end is fed through the base's top, slotted hole 12 and through the locking cylinder's hole. The cylinder's set screws are then tightened to lock the apparatus 1 in place.

The surgeon next chooses one or more of the side holes 11 for use in anchoring to secondary mounting pins which are passed through these holes 11 and into the tibia. For each of these pins, a pilot hole is initially drilled in the bone and a secondary mounting pin is inserted through the hole 11. A set screw 11a is again used to lock the apparatus 1 to each of these secondary mounting pin.

Once the apparatus 1 is securely locked to the mounting pins, the shelf 24 of the apparatus can be further adjusted and aligned to ensure that it is properly located to most effectively assist the surgeon in making the necessary cuts. The exact location of the apparatus 1 on the tibia and the alignment of the apparatus' shelf 24 are precisely noted withh the aid of the various alignment and orienthation scales that exist on the apparatus. This information is critical to assist in properly locating the apparatus 1 on the cadaver where the duplicate cuts will be made.

In addition to the usefulness of this apparatus in ankle allografts, it has been found that this apparatus is also useful in other orthopedic surgical procedures where it is useful to cut bones withh other than a straight cut. For example, this apparatus is useful in performing a high tibial osteotomy.

Although the foregoing disclosure relates to a preferred embodiment of the invention, it is understood that these details have been given for the purposes of clarification only. Various changes and modifications of the invention will be apparent, to one having ordinary skill in the art, withhout departing from the spirit and scope of the invention as hereinafter set forth in the claims.

We claim:

1. An apparatus that is secured for use with anchoring pins so as to facilitate a surgical procedure where a bone is cut so as to resect a portion of the outer surface of said bone so that the remaining cut portion of said bone has a prescribed degree of curvature, said apparatus comprising:

a base having a top and a bottom surface and a primary anchoring hole that extends between said surfaces and through which a primary anchoring pin may be extended for anchoring with said bone, said anchoring hole having an adjoining and cooperating primary means for locking the position of said base relative to said anchoring pin, said base further having a secondary anchoring hole that extends from the top to the bottom of said base and through which a secondary anchoring pin may be extended for anchoring with said bone, said secondary anchoring hole having an adjoining and cooperating secondary means for locking the position of said base relative to said anchoring pin, said base further having a front surface which contains an opening, a surgical blade positioning means, said means having a front and a rear surface, said front surface configured to have said prescribed degree of curvature and to allow a surgeon to position a surgical blade for making the cut having prescribed degree of curvature, and a shaft having distal and proximate ends, said shaft distal end being attached to said positioning means rear surface, the proximate end of said shaft configured so as to allow said shaft to slide in and out from said base opening for positioning said front surface of surgical blade positioning means at a prescribed position in front of said base front surface.

2. An apparatus as recited in claim 1, wherein:
said surgical procedure involves the replacement of ankle tissue between the bottom of the tibia and the adjoining top of the talus bone,
said anchoring pins being anchored in the tibia, and
said prescribed degree of curvature in front surface of said surgical blade positioning means is approximately that of the curvature observable in the dome or top portion of the talus.

3. An apparatus as recited in claim 1, wherein said secondary locking means having a threaded, set screw hole in said base and a set screw positioned in said hole that may be screwed so as to cause the tip of said screw to come into contact with said secondary anchoring pin.

4. An apparatus as recited in claim 1, wherein:
said shaft proximate end being round so that said shaft may rotate in said base opening, and
said attachment of said shaft to said rear surface of said surgical blade positioning means having a pivot connection so that said means may pivot with respect to said shaft, said attachment further having a means for locking said shelf at any one of the positions attainable by pivoting said surgical blade positioning means.

5. An apparatus as recited in claim 1, wherein said primary anchoring hole being slotted so as to allow for same additional flexibility in the angle at which said anchoring pin enters said hole.

6. An apparatus as recited in claim 3, wherein said primary anchoring hole being slotted so as to allow for same additional flexibility in the angle at which said anchoring pin enters said hole.

7. An apparatus as recited in claim 4, wherein:
said base comprising a rear surface having a slotted cavity that extends toward the front of said base and intersects the path of said primary anchoring hole,
said base further having a cylinder that is configured to fit within said slotted cavity, said cylinder having an axial bore and a radial hole thru said cylinder, wherein said axial bore extending from the rear of said cylinder towards its front, said axial bore intersecting said radial hole, wherein said radial hole is configured so as to allow said primary anchoring pin to be fitted through said radial hole, said axial bore containing a set screw that is used to lock the relative position of said primary anchoring pin passing through said cylinder radial hole, and
said base further having a means for locking the position of said cylinder in said cavity.

8. An apparatus as recited in claim 6, wherein:
said base comprising a rear surface having a slotted cavity that extends toward the front of said base and intersects the path of said primary anchoring hole,
said base further having a cylinder that is configured to fit within said slotted cavity, said cylinder having an axial bore and a radial hole thru said cylinder, wherein said axial bore extending from the rear of said cylinder towards its front, said axial bore intersecting said radial hole, wherein said radial hole is configured so as to allow said primary anchoring pin to be fitted through said radial hole, said axial bore containing a set screw that is used to lock the relative position of said primary anchoring pin passing through said cylinder radial hole, and
said base further having a means for locking the position of said cylinder in said cavity.

9. An apparatus as recited in claim 1, wherein the location of said secondary anchoring hole being a specified distance away from the longitudinal centerline of said base, the centerline of said secondary anchoring hole being slanted towards and at an angle with respect to the base's longitudinal centerline.

10. An apparatus as recited in claim 6, wherein to location of said secondary anchoring hole being a specified distance away from the longitudinal centerline of said base, the centerline of said secondary anchoring hole being slanted towards and at an angle with respect to the base's longitudinal centerline.

11. A method for facilitating a surgical procedure where it is desired to cut a bone so as to resect a portion of the outer surface of said bone so that the remaining cut portion of said bone has a prescribed degree of curvature, said method comprising the steps of:
providing a base for attachment to said bone,
removably attaching said base to said bone,
providing an interchangeable, surgical blade positioning means for attachment to said base,
configuring said surgical blade positioning means so that it has a front surface configured to have said prescribed degree of curvature and to allow a surgeon to position a surgical blade for making the cut having prescribed degree of curvature, and
attaching said surgical blade positioning means to said base in such a manner so as to provide flexibility in the orientation of said front surface of said surgical blade positioning means.

12. A method as recited in claim 11, wherein:
said surgical procedure involves the replacement of ankle tissue between the bottom of the tibia and the adjoining top of the talus bone,
said prescribed degree of curvature in front surface of said surgical blade positioning means is approximately that of the curvature observable in the dome or top portion of the talus.

13. A method as recited in claim 12, further comprising the steps of:
providing said base with a primary anchoring hole that extends from the top to the bottom of said base and through which an anchoring pin may be extended for anchoring with said bone,
providing said primary anchoring hole with an adjoining and cooperating means for locking the position of said base relative to said anchoring pin,
providing said base with a secondary anchoring hole that extends from the top to the bottom of said base and through which an anchoring pin may be extended for anchoring with said bone,
providing said secondary anchoring hole with an adjoining and cooperating means for locking the position of said base relative to said anchoring pin,
providing said base with an opening in its front surface, and
providing the rear surface of said surgical blade positioning means with a shaft which slides in and out from said base opening for positioning said front surface of surgical blade positioning means at a prescribed position in front of said base front surface.

14. A method as recited in claim 13, further comprising the step of:
providing said shaft with an exterior surface that is round so that said shaft may rotate in said base opening, and
providing the rear surface of said surgical blade positioning means with a pivot connection so that said surgical blade positioning means may pivot with respect to said shaft, said pivot connection having a means for locking said surgical blade positioning means at any one of the positions attainable by pivoting said surgical blade positioning means.

15. A method as recited in claim 14, further comprising the step of:

configuring said primary anchoring hole so that it is slotted to allow for additional flexibility in the angle at which said anchoring pin enters said primary anchoring hole.

16. A method as recited in claim 15, further comprising the step of:

locating said secondary anchoring hole a specified distance away from the longitudinal centerline of said base, the centerline of said hole being slanted towards and at an angle with respect to the base's longitudinal centerline so as to allow an anchoring pin that passes through said hole to approximately contact the tibia perpendicularly to its surface.

* * * * *